United States Patent
Herting et al.

(10) Patent No.: US 6,656,962 B2
(45) Date of Patent: *Dec. 2, 2003

(54) USE OF AMINO-ISOXAZOLIDONE COMPOUNDS FOR IMPROVEMENT OF LEXICAL PRIMING

(75) Inventors: Robert L. Herting, Park Ridge, IL (US); Barbara L. Schwartz, Washington, DC (US); Stephen I. Deutsch, Silver Spring, MD (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/154,478

(22) Filed: May 23, 2002

(65) Prior Publication Data

US 2002/0183373 A1 Dec. 5, 2002

Related U.S. Application Data

(62) Division of application No. 09/793,661, filed on Feb. 26, 2001, now Pat. No. 6,420,404, which is a continuation of application No. 09/571,962, filed on May 16, 2000, now abandoned, which is a continuation of application No. 09/375,698, filed on Aug. 16, 1999, now abandoned, which is a continuation of application No. 09/110,731, filed on Jul. 6, 1998, now abandoned, which is a continuation of application No. 08/852,373, filed on May 20, 1997, now abandoned, which is a continuation of application No. 08/344,431, filed on Nov. 23, 1994, now abandoned.

(51) Int. Cl.[7] .............................. A61K 31/42
(52) U.S. Cl. ...................................... 514/380
(58) Field of Search ......................... 514/380

(56) References Cited

U.S. PATENT DOCUMENTS

| 4,904,681 | A | 2/1990 | Cordi et al. ............... 514/380 |
| 5,061,721 | A | 10/1991 | Cordi et al. ............... 514/376 |
| 5,087,633 | A | 2/1992 | Cordi et al. ............... 514/380 |
| 5,187,171 | A | 2/1993 | Cordi ............................ 514/359 |
| 5,260,324 | A | 11/1993 | Cordi et al. ............... 514/376 |

OTHER PUBLICATIONS

Monahan et al, *Pharmacology, Biochem. and Behavior, 34*, 649–653(1989).
Kleckner et al, *Science, 241*, 835–837(1988).
Hood et al, *Neuroscience Letters, 98*, 4627–4636 (1989).
Baxter et al, *Neurobiol. of Aging, 15*, 297–313 (1994).
Jones et al, *Annals of N.Y. Acad.Sci., 640*, 241–244 (1991).
Wesnes et al, *Human Psychopharmacology, 3*, 27–41 (1988).
Schwartz et al, *Neurology, 41*, 1341–1343 (1991).
Mayer et al, *Arzneim.Forsch., 21(2)*, 835–837(1988).
M. Vojtechovsky, *Act. Nerv. Super., 7(3)*, 269 (1965).
Vitek et al, *Psychopharmacologia, 7(3)*, 203–219 (1965).
G.E. Crane, *Compr. Psychiat.,2*, 51–53, (1961).
Simeon et al, *Compr. Psychiat., 11*, 80–88, (1970).

*Primary Examiner*—Phyllis G. Spivack
(74) *Attorney, Agent, or Firm*—J. Timothy Keane; Joseph R. Schuh

(57) ABSTRACT

A class of amino-isoxazolidone compounds is described for use to improve lexical priming in patients susceptible to or afflicted with Alzheimer's Disease. Preferred compounds of this class are D-cycloserine and its prodrugs.

6 Claims, 2 Drawing Sheets

USE OF AMINO-ISOXAZOLIDONE COMPOUNDS FOR IMPROVEMENT OF LEXICAL PRIMING

RELATED APPLICATIONS

This is a divisional of pending U.S. application Ser. No. 09/793,661 filed Feb. 26, 2001, now U.S. Pat. No. 6,420,404, which is a continuation of application Ser. No. 09/571,962 filed on May 16, 2000, now abandoned, which is a continuation of application Ser. No. 09/375,698, filed on Aug. 16, 1999, now abandoned, which is a continuation of application Ser. No. 09/110,731, filed Jul. 6, 1998, now abandoned, which is a continuation of application Ser. No. 08/852,373, filed on May 20, 1997, now abandoned, which is a continuation of application Ser. No. 08/344,431, filed on Nov. 23, 1994, now abandoned.

FIELD OF THE INVENTION

This invention is in the field of clinical neurology and relates specifically to compound, formulations and methods for use in improving implicit memory, particularly in patients afflicted with or susceptible to Alzheimer's Disease.

BACKGROUND OF THE INVENTION

L-Glutamate is one of the major excitatory neurotransmitters in the central nervous system. Over the past decade, evidence has been accruing that the N-methyl-D-aspartate (NMDA) subtype of glutamate receptor is involved in processes of learning and memory [J. B. Monahan et al, *Pharmacology, Biochemistry and Behavior,* 34, 649–653 (1989)]. As a result, the NMDA receptor complex has become a target site for the development of pharmacological agents to treat memory disorders associated with aging and dementia.

One concern in the development of therapeutic agents is that agents potentiating NMDA-type glutamate activity can overstimulate neurons, which leads to excitotoxity and eventual cell death. However, the recent discovery of the glycine-B site on the NMDA receptor complex has provided an avenue for drugs to modulate glutamate activity [N. W. Kleckner et al, *Science,* 241, 835–837 (1988)]. In the presence of glutamate, glycine increases the likelihood that glutamate will be effective in promoting channel opening allowing positively charged ions to flow into the nerve cell, thereby exciting the cell. One drug that acts at the glycine modulatory site is the partial glycine agonist D-cycloserine [W. F. Hood et al, *Neuroscience Letters,* 98, 91–95 (1989)]. At "low" concentrations, D-cycloserine behaves as an agonist mimicking glycine's effects, whereas at "higher" concentrations it can antagonize the effects of endogenous glycine. The antagonist property of D-cycloserine can prevent excess stimulation of the neuron, thereby preventing excitotoxicity.

Recent findings have shown that D-cycloserine ameliorates learning and memory deficits associated with normal aging [M. G. Baxter et al, *Neurobiology of Aging,* 15, 297–213 (1994)] and drug-induced amnesia [R. W. Jones et al, *Annals of the New York Academy of Science,* 640, 241–244 (1991)]. These findings are of particular importance to the treatment of memory disturbances found in Alzheimer's disease [K. Wesnes et al, *Human Psychopharmacology,* 3, 27–41 (1988)]. For instance, administration of scopolamine, a cholinergic blocker, to healthy human subjects produces reversible memory deficits that resemble those found in Alzheimer's disease [K. Wesnes et al, Ibid.]. D-cycloserine has been shown to alleviate a variety of scopolamine-induced deficits for recently presented items [R. W. Jones et al, Ibid.]. For example, D-cycloserine can improve deficient recall and recognition performance in young adults and recognition performance in older adults [R. W. Jones et al, Ibid.].

It has been shown that the compound milacemide, acting at the glycine site, facilitates word retrieval in healthy young and older adults [B. L. Schwartz et al, *Neurology,* 41, 1341–1343 (1991)].

Amino-oxazolidone compounds have been investigated for CNS effects. For example, the compound D-cycloserine, in its D- and L-isomer forms, has been evaluated for CNS effects in animals [O. Mayer et al, *Arzneim. Forsch.,* 21(2), 298–303 (1971)]. These cycloserine isomers have also been evaluated for psychological and physiological effects in human subjects. For example, D-cycloserine when administered at 500 mg/day doses to healthy human subjects, appeared to stimulate slight sociability, but with depressed mental alertness [M. Vojtechovsky, *Act. Nerv. Super.,* 7(3), 269 (1965)]. Also, D-cyloserine has been administered at 1000 to 1500 mg/day to healthy volunteers whose blood levels showed increased levels of monoamine oxidase enzyme activity [V. Vitek et al, *Psychopharmacologia,* 7(3), 203–219 (1965)].

D-cycloserine has been investigated as a therapeutic agent for mental disorders in clinical trials, wherein D-cycloserine was administered to mentally disturbed patients at doses of 500 mg per day [G. E. Crane, *Compr. Psychiat.,* 2, 51–53 (1961)]. In such clinical trials, improvements in depression, insomnia, anexoria or tension were found for some patients, while patients suffering from severe neurosis or psychosis responded poorly to such medication. Moreover, D-cycloserine has been used to exacerbate the symptoms of schizophrenia in an attempt to cure the ailment by symptom provocation [J. Simeon et al, *Compr. Psychiat.,* 11, 80–88 (1970)]. It appears that D-cycloserine, at the dose levels used in these studies, is acting as an antagonist at the glycine site of the NMDA-PCP receptor complex mimicking the action of PCP by inducing psychosis.

Other CNS-related investigations have been conducted with amino-oxazolidone compounds for interactions with the NMDA receptor complex. For example, U.S. Pat. No. 4,904,681 issued on Feb. 27, 1990 to A. A. Cordi et al describes evaluation of D-cycloserine as a glycine B partial agonist interacting with the NMDA receptor complex for treatment of learning or memory dysfunctions or for enhancement of cognitive functions. U.S. Pat. No. 5,061,721 issued on Oct. 29, 1991 to A. A. Cordi et al describes methods of treating Alzheimer's Disease, age-associated memory impairment, learning deficit and psychotic disorders, as well as methods for improving memory or learning in healthy subjects, using a composition containing a mixture of D-cycloserine and D-alanine. U.S. Pat. No. 5,087,633 issued on Feb. 11, 1992 to A. A. Cordi et al describes use of a glycine B partial agonist for memory and learning enhancement or treatment of a cognitive disorder. U.S. Pat. No. 5,187,171 issued on Feb. 16, 1993 to A. A. Cordi describes D-cycloserine as a glycine B partial agonist interacting with the NMDA receptor complex for treatment of psychotic conditions. U.S. Pat. No. 5,260,324 issued on Nov. 9, 1993 to A. A. Cordi et al describes compositions containing D-cycloserine with a side-effecting reducing amount of D-alanine, in a ratio range of about 1-to-1 to about 100-to-1 of D-alanine to D-cycloserine, for use in learning-memory enhancement or treatment of a cognitive psychotic disorder. U.S. patent application Ser. No. 08/155,986 filed on Nov. 22, 1993 of M. Nevins describes use of D-cycloserine for treatment of anxiety.

DESCRIPTION OF THE INVENTION

Figure 1:
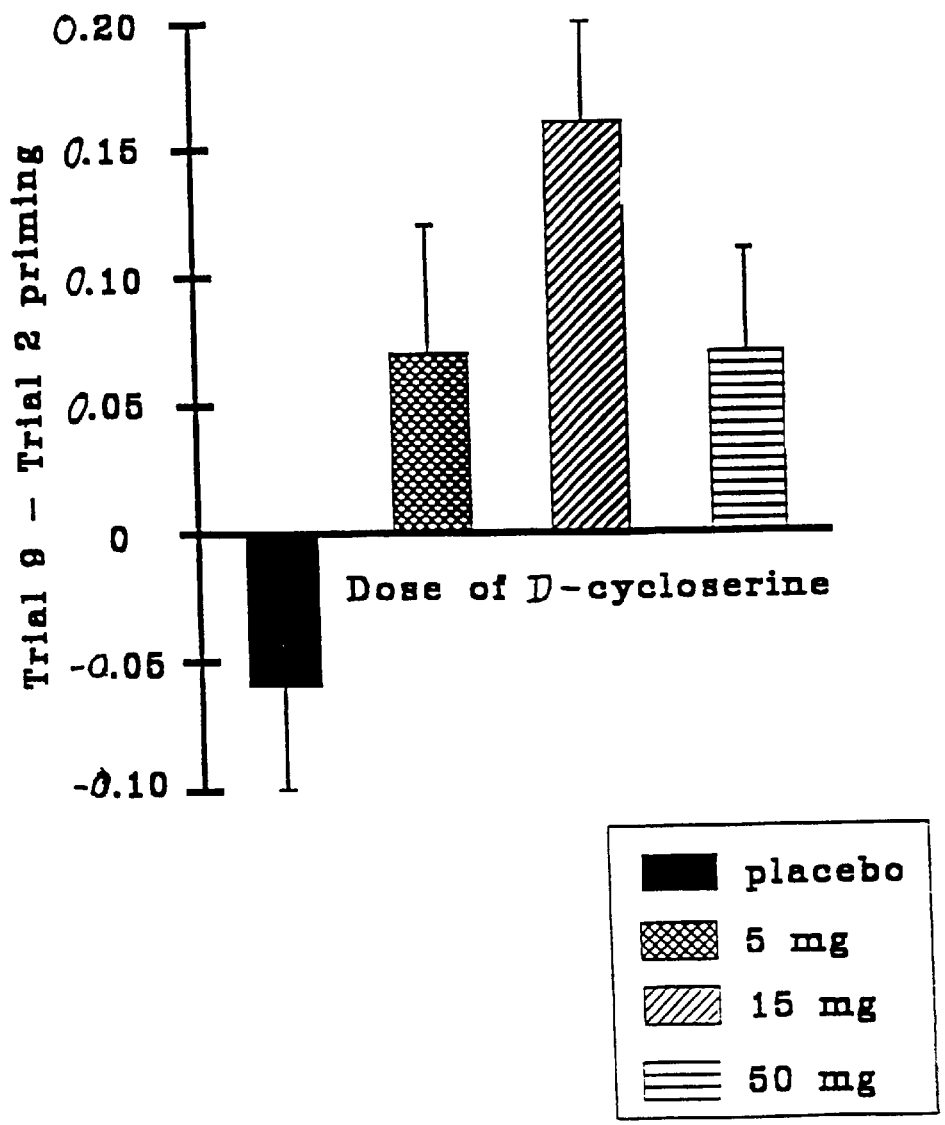
FIG. 1 describes increase in priming (learning) for patients who received placebo, 5 mg, 15 mg, and 50 mg of D-cycloserine twice daily.

Improvement of implicit memory in a subject susceptible to or afflicted with impairment of implicit memory, especially in a subject having Alzheimer's Disease, is achieved by administering to the subject a therapeutically-effective amount of a glycine B partial agonist. A glycine B partial agonist for such treatment may be provided by one or more amino-isoxazolidone compounds, or a prodrug thereof, selected from a family of compounds of Formula I:

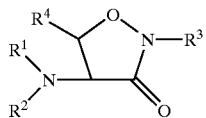
(I)

wherein $R^1$ is selected from hydrido, alkyl, haloalkyl, alkoxyalkyl, cycloalkyl, aralkyl and aryl; wherein each of $R^2$ and $R^3$ is independently selected from hydrido, alkyl, aralkyl, aryl,

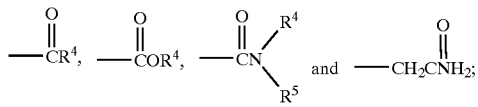

wherein $R^1$ and $R^2$ may be taken together to form a Schiff-base derived group selected from derivatives of aldehydes and ketones; wherein each of $R^4$ and $R^5$ is independently selected from hydrido, alkyl, haloalkyl, alkoxyalkyl, cycloalkyl, aralkyl and aryl; or a pharmaceutically-acceptable salt thereof. Where compounds of Formula I exist as optical isomers, the D-configuration is generally preferred.

A preferred family of compounds consists of compounds wherein $R^1$ is selected from hydrido, lower alkyl, haloalkyl, cycloalkyl, alkoxyalkyl, phenalkyl and phenyl; wherein each of $R^2$ and $R^3$ is independently selected from hydrido, lower alkyl, phenalkyl, phenyl,

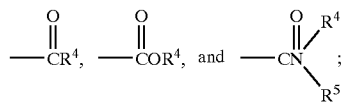

wherein the Schiff-base derived group is derived from acetylacetone, salicylaldehyde, benzophenone derivatives and acetylacetic acid esters; and wherein each of $R^4$ and $R^5$ is independently selected from hydrido, lower alkyl, phenyl and benzyl.

A more preferred group of compounds within Formula I consists of these compounds wherein $R^1$ is hydrido; wherein each of $R^2$ and $R^3$ is independently selected from

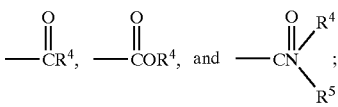

wherein the Schiff-base derived group is selected from

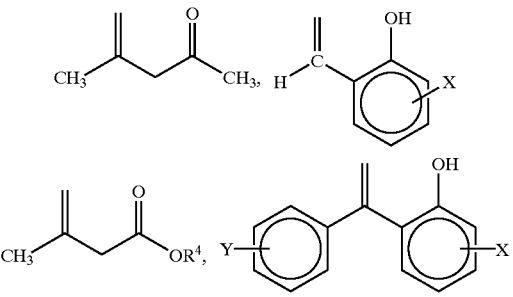

wherein each of X and Y is independently one or more groups, substitutable at a substitutable position, selected from hydrido, lower alkyl and halo; and wherein each of $R^4$ and $R^5$ is independently selected from hydrido, lower alkyl and phenyl.

A most preferred group of compounds within Formula I consists of those compounds wherein $R^1$ is hydrido; wherein the Schiff-base derived group is selected from

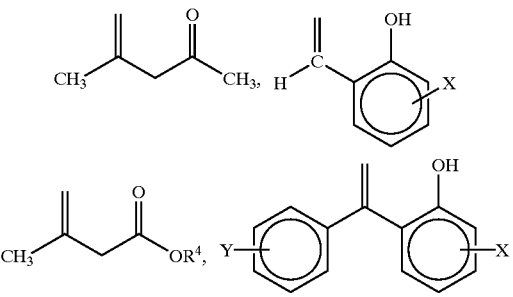

wherein each of X and Y is independently selected from fluoro, chloro and bromo; and wherein each of $R^2$, $R^3$ and $R^4$ is hydrido.

A most preferred specific compound of Formula I is the compound 4-amino-3-isoxazolidone having the structural formula

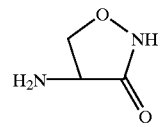

This compound exists in the L- and D-isomeric forms, of which the compound D-cycloserine is most highly preferred.

Also embraced by Formula I are the tautomeric forms of these compounds as represented by Formula II:

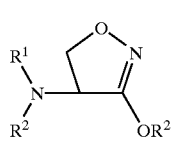

(II)

wherein $R^1$, $R^2$ and $R^3$ are as defined for the compounds of Formula I.

The term "hydrido" denotes a single hydrogen atom (H) which may be attached, for example, to a carbon atom to form a hydrocarboyl group (—CH—); or the hydrogen atom may be attached to an oxygen atom to form a hydroxyl group (—OH). Where the term "alkyl" is used, either alone or within another term such as "haloalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, and preferably having three to about five carbon atoms, such as cyclopropyl and cyclobutyl. The term "haloalkyl" embraces radicals wherein any one or more of the alkyl carbon atoms is substituted with one or more halo groups, preferably selected from bormo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkoxy" and "alkoxyalkyl" embrace linear or branched oxy-containing radicals having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "aralkyl" is exemplified by "phenalkyl" of which benzyl is a specific example.

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl.

Included within the family of compounds of Formulas I and II are the isomeric forms of the described compounds including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I and II contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I and II.

The term "prodrug", as used herein, embraces compounds which are precursors of glycine B partial agonists. Such precursor compounds can release the glycine B partial agonist by some chemical or enzymatic reaction taking place in the body or, optimally, in the brain.

Compounds of Formula I and Formula II can be synthesized by methods described in the literature. For example, syntheses of N-acyl derivatives and Schiff-base derivatives of D-cycloserine are described by N. P. Jensen et al, *J. Med. Chem.*, 23 6–8 (1980). Syntheses of N,N'-diacyl derivatives of cycloserine are described by J. C. Howard, *J. Org. Chem.*, 46, 1720–1723 (1981). Syntheses of alkyl derivatives of cycloserine are described by C. H. Stammer, *J. Med. Chem.*, 13(6), 1013 (1970). Synthesis L- and D-isomers of cycloserine, as well as analogues thereof, are described by P. A. Plattner et al, *Helv. Chim. Acta.*, 40, 1531 (1957).

Biological Evaluation

Assay A: Glycine Binding Assay Procedure

Synaptic plasma membranes (SPM) were prepared from rat forebrain and stored as previously described [J. B. Monahan and J. Michel, *J. Neurochem.*, 48, 1699–1708 (1987)]. Frozen membranes were thawed and diluted 1:20 with 0.04% triton X-100 in 50 mM tris/acetate (pH 7.4). Following incubation at 37° C. for 30 min., the SPM were collected by centrifugation at 95,000×g for 15 min. The pellet was resuspended in 50 mM tris/acetate (pH 7.4, triton-free) and handhomogenized five times. The membranes were again centrifuged as above. The pellet was washed two additional times with 50 mM tris/acetate (without homogenization) and centrifuged. The final pellet was resuspended with homogenization in 50 mM tris/acetate.

In the general receptor binding assay procedure, 10 nM [3H]glycine was added to the appropriate concentration of the test compounds and the assay initiated by the addition of 0.2–0.4 mg of ice cold SPM. The assay, which was done in 1.5 ml centrifuge tubes, was adjusted to a total volume of 1.0 ml with all additions being made in 50 mM tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25–35% of the total binding. The binding of [3H]glycine to the SPM was analyzed using Scatchard and Hill transformations and the Ki for other compounds was determined using logit-log analysis. Calculations and regression analysis were performed using templates developed for Lotus 123 as previously described.

| Result | $K_i$ ($\mu$M) |
|---|---|
| Glycine | 0.18 |
| D-cycloserine | 1.92 |
| L-cycloserine | >100 |

Assay B: TCP Modulation Assay

[3H]TCP binding was performed using Triton X-100 washed synaptic plasma membranes (SPM) prepared from rat forebrain (30–45 day old, male SpragueDawley; Sasco, St. Charles, Mo.) as described previously [J. W. Thomas, W. F. Hood, J. B. Monahan, P. C. Contreras and T. L. O'Donohue, *Brain Res.*, 442, 396–398 (1988)]. The assay was initiated by the addition of SPM (0.15–0.25 mg) to an incubation containing 2.0 nM [3H]TCP (47.1 Ci/mmole; New England Nuclear, Boston, Mass.) and various concentrations of the appropriate test compound in a total volume of 0.5 ml (all additions were made in 5 mM Tris/HCl buffer, pH 7.4) and continued for 60 min at 25° C. The samples were then filtered through glass fiber filters (Schleicher and Schuell #32) which were pretreated with 0.05% (v/v) polyethylenimine. The filters were washed and the radioactivity quantitated by liquid scintillation spectrometry. Stimulation of [3H]TCP binding was measured as an increase in basal specific binding (basal binding=2583+381 DPM and this value increased to a maximum of 4712+779 DPM in the presence of 0.6 $\mu$M glycine) with nonspecific binding as the residual binding in the presence of 60 $\mu$M PCP (562+30 DPM). The $K_d$ for [3H]TCP under basal conditions was 44 nM. The $EC_{50}$ values for the stimulation of [3H]TCP binding were determined using a four parameter logistic regression analysis.

D-cycloserine stimulates basal [3H]TCP binding in a dose dependent manner with an $EC_{50}$=19.7 $\mu$M. Previous data show that D-cycloserine interacts with the NMDA-associated [3H]glycine recognition site ($K_i$=2.33+0.29 $\mu$M). No affinity for the NMDA recognition site, however, was detected as evidenced by the lack of displacement of NMDA-specific L-[3H]glutamate binding ($K_i$>100 $\mu$M). This finding indicates that D-cycloserine enhances [3H]TCP binding through its interaction with the NMDA receptor-associated glycine recognition site (herein defined as the "Glycine B receptor"). The maximal stimulation produced by D-cycloserine, however, was significantly less than that produced by both glycine and D-serine.

This apparent lower efficacy indicates the potential partial agonist character of D-cycloserine which was confirmed by the following experiment. In the absence of exogenously added glycine, D-cycloserine has agonist properties and stimulates [3H]TCP binding to a maximum of 40–50% of the stimulation induced by glycine alone. However, in the presence of various concentrations of glycine (0.1–0.6 $\mu$M), D-cycloserine has an apparent antagonist character and reduces the maximal level of glycine stimulation. From data developed to provide a family of D-cycloserine dose-response curves (generated in the presence of several fixed concentrations of glycine), it has been observed that such dose-response curves asymptotically approach 40–50% of the maximal stimulation induced by glycine alone, a pattern characteristic of compounds with partial agonist properties as is known with different compounds acting on other receptors.

Further confirmation of the partial agonist character of D-cycloserine was demonstrated in experiments wherein a glycine dose-response analysis was performed in the presence of several fixed concentrations of D-cycloserine (0–100 $\mu$M). D-cycloserine potentiated the glycine stimulation of [3H]TCP binding at glycine concentrations below 0.1 $\mu$M, while at higher glycine concentrations (0.1–15 $\mu$M) D-cycloserine produced a rightward shift in the dose-response curve. These results are again consistent with partial agonist characteristics.

Assay C: Implicit Memory Paradigm

Alzheimer disease is associated with loss in a variety of cognitive domains such as memory, language and visual-spatial skills. One form of memory loss associated with Alzheimer's Disease is impairment of memory referred to as implicit memory. Tests of implicit memory differ from standard methods of assessing memory in which subjects are asked to recall or recognize recently presented words, pictures or faces. With implicit tests, subjects need not refer to previously experienced events to perform the tests. Memory is inferred from the facilitative effects on performance produced by prior exposure to study items. The recent intensive investigation of implicit memory in Alzheimer's disease reveals that these patients are impaired on several tests, such as those that require patients to identify perceptually degraded pictures of objects, [M. W. Bondi et al, *J. Clin. & Exp. Neuro.* 13, 339–358 (1991)], retrieve a word to an incomplete letter cue (e.g., MOT__:MOTEL) [W. C. Heindel et al, Brain and Cognition, 13, 282–295 (1990)], or produce semantic associates (e.g., BIRD-:ROBIN) [D. P. Salmon et al, *Clin. & Exp. Neuro.*, 10, 477–494 (1988)]. On these tests, Alzheimer patients do not show the same benefit from prior exposure to pictures or words that is shown by normal individuals. Such deficits on implicit tests may be related to disruptions in the organization of stored knowledge or in the ability to retrieve word names and concepts from memory. Therefore, deficits in implicit memory could manifest themselves as problems in word finding and other language and memory problems observed in Alzheimer patients.

For the present invention a word identification test was used to evaluate memory in Alzheimer patients treated with D-cycloserine using procedures described by B. L. Schwartz et al, *Exp. Psych.: Learning, Memory and Cognition*, 17, 1177–1187 (1991). In this test, subjects identify words presented in a visually degraded or masked format in which only parts of each letter are shown. Subjects view several lists of these degraded words over a period of three days, some of which are repeated from day-to-day and some that are new. Learning, or what is referred to as "priming", is shown on this test when subjects identify a larger number of repeated or old words than new words. It has been reported in a similar word identification test that the level of priming in Alzheimer patients did not increase with additional repetitions of a word [A. L. Ostergaard, *Quarterly J. Psych.*, 47A, 331–364 (1994)]. The goal of the present test is to determine whether D-cycloserine improved the level of priming that occurs over trials when the same word is repeated on multiple occasions.

Patients and Methods

Patients were 108 males and females who fit eligibility criteria and had a care giver to ensure compliance with the protocol. The diagnosis of probable Alzheimer's disease was made according to the criteria defined by the National Institute on Neurological Disorders and Stroke Work Group [G. McKhann et al, *Neurology*, 34, 939–944 (1984)]. This diagnosis was based on clinical evaluation that included neuropsychological assessment, laboratory blood screening, neurolgical examination, and either a CT or MRI scan. The criteria for entry into the study was Mini-mental State Examination score between 12 and 24 inclusive [M. Folstein et al, *J. Psych. Res.*, 12, 189–198 (1975)], Global Deterioration Scale score between 3 and 5 inclusive [B. Reisberg et al, *Am. J. Psych.*, 139, 1136–1139 (1982)], Modified Hachinski, ischemic score of 4 or less [G. W. Small et al, *J. Clin. Psych.*, 46, 514–517 (1965)], and Hamilton Psychiatric Rating Scale for Depression score of 17 or less [M. Hamilton, *Neurology and Neurosurgery*, 23, 56–62 (1960)]. Patients with medical, neurological, or psychiatric illnesses other than Alzheimer's disease that could account for the abnormal mental status were excluded. Patients who required concurrent use of medications affecting the central nervous system also were excluded. The eligibility of patients was assessed during a 28-day period before the study began. All patients or their legal guardians signed an informed consent to participate in this study.

The study was conducted at multiple centers in the United States and Canada and was designed as a double-blind, parallel group comparison that included a placebo control group. According to their order of entry into the study, patients were assigned to one of three active treatments (5 mg, 15 mg, or 50 mg D-cycloserine administered twice daily) or a placebo treatment using a computer-generated randomization schedule. The first phase of the study was a seven-day period during which all eligible patients received a placebo. The second phase of the study was the double-blind treatment phase, in which patients received an oral dose of medication twice daily, in the morning and in the evening before meals. All unused medication was returned and counted to check for compliance in taking the drug.

Patients performed the word identification test during the tenth week of the double-blind treatment phase. The test was administered on three consecutive days using an IBM-compatible computer. Three learning trials were given on each of the three days for a total of nine trials. Every trial consisted of 12 degraded words that were repeated across the nine trials (old words) and 12 new words. Patients were instructed to identify each word by saying it aloud. Each trial of the test was followed by approximately 10 minutes of a non-verbal activity.

Results

Of the 108 patients who consented to participate in this study of implicit memory, 91 provided complete sets of data for the three days of testing. All analyses reported in the paper were performed using the SPSS (Windows) statistical package. The significance level was set at 0.05 for all statistical tests, unless otherwise specified. Demographic features and neuropsychological test results for patients in each treatment condition are shown in Table I. A one-way analysis of variance (ANOVA) performed on ages, years of education completed, Minimental State Exam scores, and Dementia Rating scores revealed that there were no significant differences among the four treatment groups for these variables [S. Mattis, Odessa, Fla.:Psychological Assessment Resources (1988)].

FIG. 1 shows the total increase in priming across the trials for patients in the placebo, 5 mg, 15 mg, and 50 mg groups. The total increase in priming was calculated by first deriving the amount of priming that occurred on each trial (i.e., difference in the proportion of old and new words identified). Then, the proportion of priming on trial 2 was subtracted from the proportion of priming on trial 9 to reflect the overall change in priming with the repetition of words over trials. Priming is not calculated on trial 1 because from the patient's perspective there are no old words on trial 1; the words begin to repeat on the second trial.

A one-way ANOVA performed on the total priming scores yielded a significant effect of treatment group [$F(3, 87)=4.25, p=0.01$)]. It appears from the data that all doses of the drug were associated with improvement in priming over the trials. Post-hoc Scheffe tests revealed a significant difference in performance between the 15 mg and placebo groups. In the 15 mg group, 68% of the patients improved their priming scores from trial 2 to trial 9, whereas in the placebo group, only 35% of the patients improved.

Figure 2:
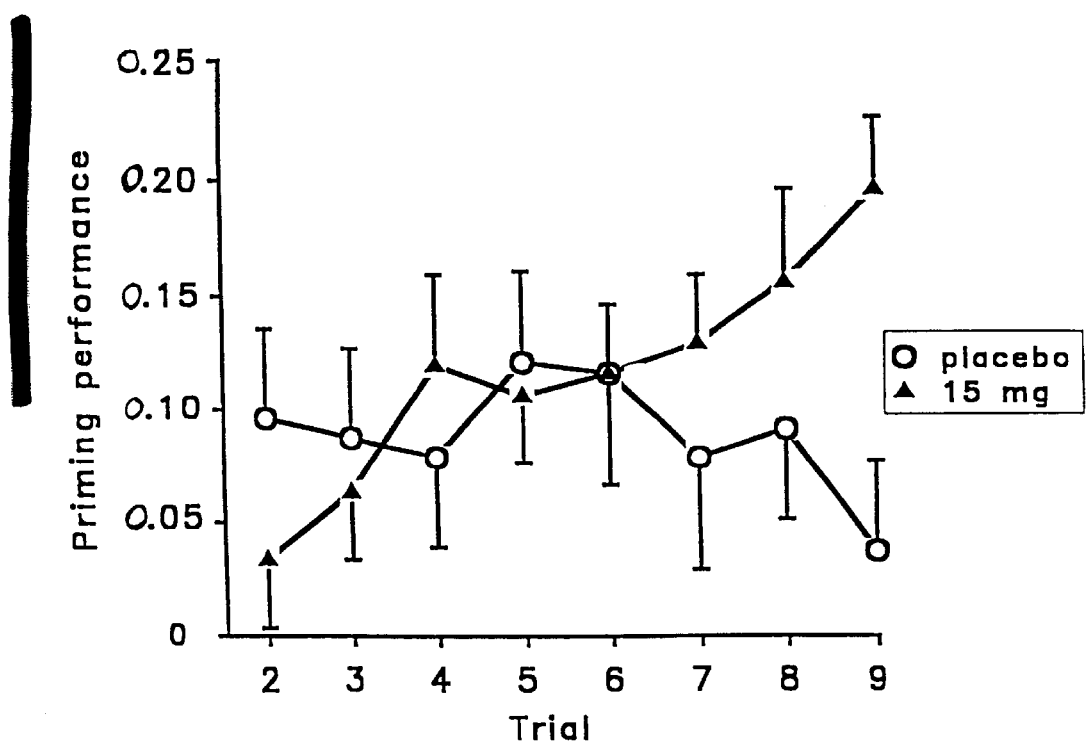
FIG. 2 describes the proportion of priming observed for patients who received either placebo or 15 mg D-cycloserine twice daily.

Trend analyses were performed to determine (a) whether there was a systematic increase in priming across trials, and (b) whether there were differences between placebo and active treatment groups in the pattern of priming across trials. A trend analysis with special contrasts was performed to test for differences between the placebo treatment and each of the three active treatments (5, 15, and 50 mg). This analysis ensures that the appropriate error term is used for each contrast. The results showed that the contrast between the placebo and 15 mg groups yielded reliable differences (see FIG. 2). There was a significant linear trend for trials [$F(1, 87)=11.78, p=0.001$] and a significant interaction of group and linear trend [$F(1, 87)=10.18, p=0.002$]. Simple effects tests of the interaction revealed that there was a significant linear trend across trials in the 15 mg group [$F(1,87)=15.06, p=0.000$)], but not in the placebo group ($F<1$).

The results of the trend analyses confirmed that the pattern of performance over trials differed for patients in the 15 mg and placebo groups. As can be seen from the data in FIG. 2, patients in the 15 mg group showed a systematic increase in priming performance from trial 2 to trial 9. In contrast, patients who received a placebo showed a relatively constant level of performance over the trials. These patients' identification performance did not benefit from multiple presentations of a word. It also can be pointed out that patients in the 15 mg group revealed no decrease in priming over the 24-hour retention intervals that occurred between trials 3 and 4 and between trials 6 and 7. These results suggest further that D-cycloserine may benefit the retention of implicitly learned information as well as the learning that occurs within each day.

Patients who received 15 mg D-cqcloserine twice daily displayed an improved ability to identify perceptually-degraded words across trials compared with those who received a placebo. These findings support a conclusion that D-cycloserine enhanced implicit learning and retention of verbal material over a three-day period. These results are consistent with prior work showing that an acute dose of 15 mg D-cycloserine was most effective in facilitating remembering in a group of healthy subjects, with the 5 mg and 50 mg doses of the drug showing non-significant trends toward improvement [R. W. Jones et al, Ibid.]

The implicit test used in this study was an experimental measure of memory rather than a clinical instrument. Use of such tests may lead to an understanding of the basic cognitive processes that are affected by these pharmacological agents. For instance, there are several cognitive mechanisms by which D-cycloserine could have influenced implicit memory. One possibility is that the drug facilitated perceptual learning. Alzheimer patients saw the same configuration of dot patterns each time a word was repeated on a trial.

D-cycloserine could have influenced the ability to learn and retain these familiar perceptual patterns over the three days of testing.

An alternative account of these findings is that D-cycloserine improved lexical priming. Alzheimer patients have relatively spared knowledge of phonological and orthographic rules of English words, as evidenced by their normal reading and normal ability to judge real words from nonwords [D. A. Balota et al, *Brain and Language*, 40, 181–201 (1991); B. A. Ober et al, *Neuropsychologia*, 26, 273–286 (1988)]. Patients may have utilized this knowledge to identify letter combinations from the perceptually-degraded cues. The drug might have enhanced patients' ability to retrieve word names for previously presented words given this partial letter information. Numerous studies with animals and humans indicate that D-cycloserine facilitates memory functions mediated by the hippocampus and related structures in the mesial temporal lobe {R. W. Jones et al, Ibid.; L. T. Thompson et al, *Nature*, 359, 638–641 (1992)]. However, priming phenomena do not depend predominantly on the hippocampal system. Recent findings from metabolic brain imaging studies and neuropsychological studies suggest instead that neocortical areas such as the temporal, parietal, and occipital areas support priming [J. D. E. Gabrieli et al, *Cortex*, 30, 75–103 (1994); L. R. Squire et al, *Proc. Nat. Acad. Sci.*, 89, 1837–1841 (1992)]. Thus, the finding that D-cycloserine facilitates priming in Alzheimer patients supports the assertion that the drug influences cognitive processes mediated by neocortical systems as well as those mediated by the hippocampal system.

In a larger study of the safety and efficacy of D-cycloserine in Alzheimer's disease, recognition memory and attentional tests were administered. However, D-cycloserine did not improve performance on these other tests [G. D. Searle & Co., Skokie, Ill. "Efficacy and safety of cycloserine in patients with Alzheimer's disease". Protocol No.: NC6-93-06-009, (1993)]. Therefore, it appears that D-cycloserine has a selective beneficial effect on implicit memory in these patients. More importantly, as to the present invention this implicit memory test shows that a drug that potentiates NMDA-mediated glutamatergic activity can improve a memory function in mild to moderately impaired patients with Alzheimer's disease.

TABLE I

Demographic Features and Neuropsychological Test Results for Treatment Groups

| | Treatment Group | | | |
| --- | --- | --- | --- | --- |
| | placebo | 5 mg | 15 mg | 50 mg |
| | Means (standard deviations) | | | |
| N | 20 | 22 | 25 | 24 |
| Male/Female | 13/7 | 14/8 | 9/16 | 13/11 |
| Age (yr) | 72.5 | 73.8 | 76.6 | 74.4 |
| | (8.8) | (8.5) | (8.4) | (8.9) |
| Education (yr) | 13.7 | 14.2 | 12.1 | 13.1 |
| | (2.7) | (3.5) | (2.4) | (2.9) |
| Mini-mental State Exam | 20.05 | 19.68 | 20.68 | 20.28 |
| | (3.3) | (3.8) | (3.1) | (3.5) |
| Dementia Rating Scale | 113.05 | 110.77 | 117.28 | 114.83 |
| | (16.76) | (16.36) | (16.25) | (12.52) |

Administration of compounds within Formulas I and II to humans can be by any technique capable of introducing the compounds into the bloodstream of a human patient, including oral administration, and by intravenous, intramuscular and subcutaneous injections.

Compounds indicated for human therapy will preferably be administered in a daily dose generally in a range, depending upon patient condition and symptomology, which is an amount therapeutically effective at the lowest possible dose, e.g. about 0.07 mg to about 0.7 mg per kilogram of body weight per day. A more preferred dosage will be a range from about 0.07 mg to about 0.4 mg per kilogram of body weight. Most preferred is a dosage in a range from about 0.1 to about 0.4 mg per kilogram of body weight per day, with a dosage of about 0.2 mg per kilogram of body weight being most highly preferred. A suitable dose can be administered in multiple sub-doses per day. These sub-doses may be administered in unit dosage forms. Typically, a dose or sub-dose may contain from about 5 mg to about 50 mg of active compound per unit dosage form per day. A further preferred dosage will contain from about 5 mg to about 25 mg of active compound per unit dosage form per day. A more preferred dosage will contain from about 10 mg to about 20 mg of active compound per unit dosage per day. Most preferred is a dosage form containing about 15 mg of active compound per unit dose per day.

The active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active agent or dispersing agent. Such capsules or tablets may contain a controlled-release formulation as may be provided by a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to improve lexical priming in a subject susceptible to or suffering from impairment of lexical priming, said method comprising administering to said subject a therapeutically-effective amount of D-4-amino-3-isoxazolidone or a pharmaceutically-acceptable salt thereof.

2. The method of claim 1 wherein said D-4-amino-3-isoxazolidone compound is administered in a daily dose range from about 5 mg to about 50 mg of said compound.

3. The method of claim 2 wherein said D-4-amino-3-isoxazolidone compound is administered in daily dose range from about 10 mg to about 40 mg of said compound.

4. The method of claim 3 wherein said D-4-amino-3-isoxazolidone compound is administered in daily dose range from about 20 mg to about 30 mg of said compound.

5. The method of claim 4 wherein aid D-4-amino-3-isoxazolidone compound is administered in a amount equivalent to a daily dose of about 30 mg of said compound.

6. A therapeutic method for treating impairment of lexical priming in a subject susceptible to or afflicted with Alzheimer's Disease when therapy is indicated, comprising administering to said subject a therapeutically-effective amount of D-4-amino-3-isoxazolidone or a pharmaceutically-acceptable salt thereof.

* * * * *